(12) United States Patent
Knap et al.

(10) Patent No.: US 6,197,566 B1
(45) Date of Patent: Mar. 6, 2001

(54) α-GALACTOSIDASE ENZYME

(75) Inventors: Inge Helmer Knap, Farum; Carsten M. Hjort, Roskilde; Torben Halkier, Frederiksberg; Lene Venke Kofod, Uggerløse, all of (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/294,923

(22) Filed: Apr. 19, 1999

Related U.S. Application Data

(62) Division of application No. 08/522,269, filed on Sep. 12, 1995, now Pat. No. 5,919,690, which is a continuation of application No. PCT/DK94/00138, filed on Mar. 30, 1994.

(30) Foreign Application Priority Data

Mar. 31, 1993 (DK) .................................... 0388/93

(51) Int. Cl.$^7$ ................ C12N 9/40; C12N 1/14
(52) U.S. Cl. ...................... 435/208; 435/256.1
(58) Field of Search ................. 435/208, 256.1

(56) References Cited

U.S. PATENT DOCUMENTS 5,296,365    3/1994    Overbeeke et al. .............. 435/208

FOREIGN PATENT DOCUMENTS

WO 86/03777    7/1986    (WO) .

OTHER PUBLICATIONS

Herder et al., Mol. Gen. Genet, vol. 233, pp. 404–410 (1992).

Bishop et al., Proc. Natl. Acad. Sci., USA, vol. 83, pp. 4859–4863 (Jul. 1986).

Bahl et al., J. of Biological Chem., vol. 244, No. 11 p. 2970–2978, 1969.

Lee et al., Archives of Biochem. & Biophysics, vol. 138, p. 264–271, 1970.

*Primary Examiner*—Elizabeth Slobodyansky
(74) *Attorney, Agent, or Firm*—Steve T. Zelson; Valeta Gregg

(57) ABSTRACT

An isolated polypeptide having α-galactosidase activity and characterized as having a pH optimum in the range of 5.0–7.0, and a temperature optimum within the range of 50–70° C. The α-galactosidase is derived from *Aspergillus niger*.

9 Claims, 6 Drawing Sheets

α-GALACTOSIDASE ENZYME

CROSS-REFERENCE TO RELATED APPLICATIONS

Figure 1:
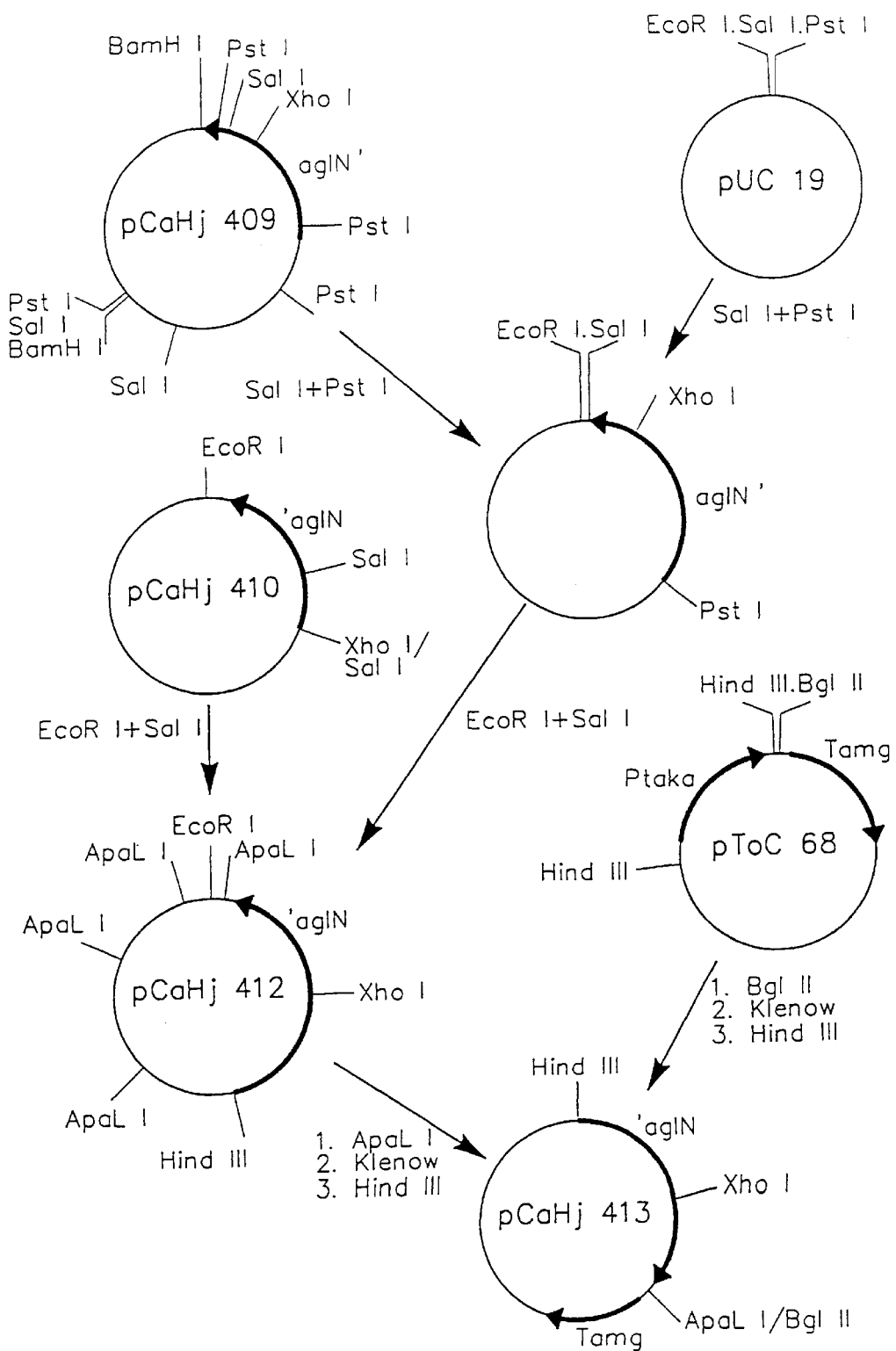

This application is a divisional of Ser. No. 08/522,269 filed Sep. 12, 1995, now U.S. Pat. No. 5,919,690 which is a 371 of PCT/DK94/00138 filed Mar. 30, 1994, which is incorporated herein by reference, which PCT application claims priority to Danish patent application DK 0388/93 filed Mar. 31, 1993.

FIELD OF THE INVENTION

The present invention relates to a DNA construct encoding an α-galactosidase enzyme and variants thereof having α-galactosidase activity, a recombinant expression vector and a cell harbouring said DNA construct, and a method of preparing an α-galactosidase enzyme preparation by use of recombinant DNA techniques. The α-galactosidase enzyme encoded by the DNA construct of the invention may, inter alia, be used for the degradation of α-galactosides present in various plant products, or as a digestive aid.

BACKGROUND OF THE INVENTION

α-galactosidase is a well-known enzyme involved in the hydrolysis of α-galactosides present in, for instance, various important plants or plant parts used for nutritional purposes such as legumes, vegetables, grains, cereals and the like. α-galactosidase enzymes are produced by various microorganisms, plants and animals. Mammals, however, are deficient in intestinal α-galactosidase production and, consequently, are incapable of decomposing ingested α-galactosides by themselves. Instead, ingested α-galactosides are decomposed by microorganisms present in the intestine. This microbial decomposition normally results in flatulence and further confers a digestive discomfort to the mammal upon ingestion of α-galactoside-containing food or feed. The physiological effects of α-galactosides are discussed in detail by Rackis, J. J., 1975.

In order to overcome the problem associated with mammalian α-galactosidase deficiency, α-galactosides contained in food or feed have been modified prior to ingestion, for instance enzymatically by the action of α-galactosidase. Alternatively, α-galactosidase has been suggested as a digestive aid, cf. WO 90/14101.

The production of α-galactosidase has been reported from bacteria, e.g. *Bacillus stearothermophilus* (U.S. Pat. No. 3,846,239), yeasts, e.g. *Saccharomyces cereviciae* (U.S. Pat. No. 4,431,737), fungi, e.g. strains of the genii Neurospora and Rhizopus (Worthington and Beuchat, 1974), *Aspergillus oryzae* (Cruz and Park, 1982), *A. ficuum* (morphologically similar *A. niger*) (Zapater et al., 1990) and *A. niger* (Bahl and Agrawal (1969 and 1972), Christakopoulos et al. (1990), Chun and Lee (1988), Jung and Lee (1986), Lee and Wacek (1970), Adya and Elbein (1976), Kaneko et al. (1991)). All of these references, however, describe the α-galactosidase production by conventional fermentation of naturally occurring or mutated microbial strains.

Overbeeke et al., 1990, describes the production of α-galactosidase from guar in *Bacillus subtilis* and Aslandis et al, 1989, describes an α-galactosidase from *E. coli*.

An *A. niger* α-galactosidase enzyme preparation (Alpha-Gal™) produced by conventional fermentation is available from Novo Nordisk A/S, Denmark. One drawback associated with the production of α-galactosidase by fermentation of *A. niger* is that substantial amounts of oxalic acid, an undesired by-product, are produced by *A. niger* simultaneously with the production of α-galactosidase.

It would be desirable to be able to produce an *A. niger* α-galactosidase enzyme preparation with reduced or without simultaneous production of oxalic acid, and further to increase the yield and the purity of the α-galactosidase preparation so produced.

The object of the present invention is to device means and methods for the production of α-galactosidase enzymes by recombinant DNA techniques. By use of such techniques it is contemplated to be possible to produce α-galactosidase in substantially larger amounts and more economical than what is possible by use of conventional fermentation technology and at the same time avoid or reduce the amount of oxalic acid formed.

BRIEF DESCRIPTION OF THE INVENTION

Accordingly, in a first aspect the present invention relates to a DNA construct comprising a DNA sequence encoding a polypeptide having α-galactosidase activity, wherein the DNA sequence a) encodes a polypeptide comprising the amino acid sequence shown in the appended SEQ ID No. 3, or b) is an analogue of the DNA sequence of a), which i) hybridizes with the DNA sequence shown in the appended SEQ ID No. 1 or 2 or an oligonucleotide probe prepared on the basis of said DNA sequence or on the basis of the amino acid sequence shown in SEQ ID No. 3 under the conditions defined below, and/or ii) encodes a polypeptide reactive with an antibody reacting with at least one epitope of a polypeptide comprising the amino acid sequence shown in the appended SEQ ID No. 3, and/or iii) encodes a polypeptide being at least 50% identical with the polypeptide having the amino acid sequence shown in the appended SEQ ID No. 3.

The nucleotide sequence shown in SEQ ID No. 1 illustrates an entire α-galactosidase gene (including introns) isolated and characterized from a strain of *Aspergillus niger*, and the nucleotide sequence shown in SEQ ID No. 2 is the corresponding cDNA sequence. The nucleotide sequences are further described in the examples hereinafter. The amino acid sequence shown in SEQ ID No. 3 is deduced from the DNA sequence shown in SEQ ID No. 2 and illustrates the amino acid sequence of the *A. niger* α-galactosidase enzyme including its signal peptide.

In a further aspect the present invention relates to a recombinant expression vector harbouring the DNA construct of the invention and a cell which either harbours the DNA construct or the expression vector of the invention.

A still further aspect of the present invention is a process for the production of a polypeptide exhibiting α-galactosidase activity, which process comprises culturing a cell as described above harbouring a DNA construct of the invention in a suitable culture medium under conditions permitting expression of the polypeptide, and recovering the resulting polypeptide from the culture.

The polypeptide exhibiting α-galactosidase activity may comprise the amino acid sequence shown in SEQ ID No. 3. or be a variant thereof. The variant may be a naturally-occurring variant derived from any source or organism, and in particular from a naturally-occurring microorganism or a mutant or derivative thereof. Furthermore, the "variant" may be a genetically engineered variant, e.g. prepared by suitably modifying a DNA sequence of the invention resulting in the addition of one or more amino acid residues to either or both the N- and C-terminal end of the polypeptide encoded by the unmodified DNA sequence, substitution of one or more amino acid residues at one or more different sites in the amino acid sequence, deletion of one or more amino acid residues at either or both ends of the polypeptide or at one or more sites in the amino acid sequence, or insertion of one or more amino acid residues at one or more sites in the amino acid sequence.

By use of the process of the invention it is possible to produce enzyme preparations having a higher content of α-galactosidase than what is possible by conventional fermentation of a parent microorganism, such as *A. niger*, inherently producing the α-galactosidase. Furthermore, the resulting α-galactosidase preparations are essentially free from any other components derived from the parent microorganism, in particular components giving rise to undesirable enzymatic side-activities. Accordingly, by use of the process of the invention it is possible to optimize the production of α-galactosidase enzyme components thereby producing an enzyme preparation with a higher specific α-galactosidase activity at lower cost than what is possible by methods known in the art. At the same time the undesirable production of oxalic acid may be substantially reduced or avoided.

DETAILED DISCLOSURE OF THE INVENTION

In the DNA construct of the invention, the analogue of the DNA sequence encoding a polypeptide having α-galactosidase activity may, for instance, be a subsequence of said DNA sequence, a genetically engineered modification of said sequence which may be prepared by well-known procedures, e.g. by site-directed mutagenesis, and/or a DNA sequence isolated from another organism and encoding an α-galactosidase enzyme with substantial similarity to the α-galactosidase having the amino acid sequence shown in SEQ ID No. 3. The actual sequence of the analogue is not critical as long as the analogue has at least one of the properties i)–iii) listed above. These properties are further discussed below.

Property i), i.e. the hybridization of a DNA sequence with the DNA sequence shown in the SEQ ID No. 1 or 2 or with a suitable oligonucleotide probe prepared on the basis of said DNA sequences or on the basis of the polypeptide shown in SEQ ID No. 3 may be carried out under any suitable conditions allowing the DNA sequences to hybridize. For instance, 1 μg of total DNA expected to harbour an analogous DNA sequence is subjected to complete digestion with, e.g. EcoRI, BamHI or HindIII, and applied to a 1% agarose gel. The DNA fragments are separated by electrophoresis, and then transferred to an Immobilon™-N membrane (Millipore Corporation) following the Manufacturers instructions. The membrane is prehybridized following the manufacturers instructions and then the DNA sequence shown in SEQ ID No. 1 or 2 or a representative fragment thereof, labelled with $32^P$ by primer extension (Sambrook et al., 1989), is added as a probe, and the temperature reduced to 45° C. After 18 hrs of hybridization the membrane is washed repeatedly in 6×SSC, 0.1% SDS at 45° C. The membrane is then subjected to autoradiography and evaluated.

Property ii), i.e. the immunological cross reactivity may be assayed using an antibody raised against or reactive with at least one epitope of the α-galactosidase enzyme comprising the amino acid sequence shown in SEQ ID No. 3. The antibody, which may either be monoclonal or polyclonal, may be produced by methods known in the art, e.g. as described by Hudson et al., 1989. The immunological cross-reactivity may be determined using assays known in the art, examples of which are Western Blotting or radial immunodiffusion assay, e.g. as described by Hudson et al., 1989.

Property iii) may be determined by comparing the amino acid sequences of the polypeptide encoded by the analogue and the polypeptide sequence shown in SEQ ID No. 3 by use of well-known algorithms, such as the one described by Lipman and Pearson (1985). In the present context, "identity" is used in its conventional meaning, i.e. intended to indicate the number of identical amino acid residues occupying similar positions in the two (or more) amino acid sequences to be compared.

It is believed that an identity of above 50% such as above about 70%, 75%, 80%, 90% and in particular above about 95% with the amino acid sequence shown in SEQ ID No. 3 is indicative for homology with the α-galactosidase encoded by the DNA sequences shown in SEQ ID Nos. 1 and 2. From an alignment study of the amino acid sequence shown in SEQ ID No. 3 and the amino acid sequence encoding the *E. coli* α-galactosidase disclosed by Aslandis et al., 1989 an identity of about 30% was found. As far as the present inventors are aware this is the only α-galactosidase with a known amino acid sequence that show any comparable identity to the α-galactosidase encoded by the DNA construct of the invention.

It is well known that homology exists between polypeptides of different origins, and α-galactosidases homologous to α-galactosidases from yeast have been found in plants as well as in mammals. Analogously herewith, it is contemplated that in the DNA construct of the invention, the DNA sequences may be derived from an animal including a mammal and an insect, a plant or a microorganism. In the present context, especially interesting origins are bacteria and fungi. The term "fungi" is intended to include yeasts and filamentous fungi.

As stated above, the DNA sequences shown in SEQ ID Nos. 1 and 2 encoding an α-galactosidase are derived from a fungus, more particularly from *A. niger*. It is contemplated that other fungal α-galactosidases may show a substantial homology, either on the DNA or amino acid level, with the *A. niger* α-galactosidase disclosed herein, and accordingly, DNA sequences of the DNA construct of the invention may be derived from a fungus, in particular from a strain of Aspergillus such as from a strain of *A. niger*. An example of such strain is the strain of *A. niger* deposited with the American Type Culture Collection under the number ATCC 16882.

When isolated from *A. niger* the α-galactosidase enzyme is contemplated to exist as a number of isoenzymes, presumably due to heavy glycosylation. It is expected that the α-galactosidase encoded by the DNA construct of the invention may be in the form of different isoenzymes, depending on the circumstances under which it is produced, and in particular on the host cell in question producing the enzyme.

In Example 1 below characteristic properties are described of an *A. niger* α-galactosidase enzyme (as isolated from *A. niger*). It has surprisingly been found that some properties of an α-galactosidase expressed from a DNA construct of the invention differ from the corresponding properties of the α-galactosidase isolated from *A. niger*.

Thus, whereas the isolated α-galactosidase has a pH optimum in the range of 3.8–6.0, the α-galactosidase expressed from the DNA sequence shown in SEQ ID No. 2 in an *Aspergillus cryzae* host cell has been found to have a pH optimum in the range of 5.0–7.0 (cf. Example 5 herinafter).

Based on the corresponding properties of the purified *A. niger* α-galactosidase, it is contemplated that an α-galactosidase enzyme encoded by the a DNA construct of the invention has a pI in the range of 4.0–5.0 (depending on the isoenzyme in question) such as about 4.3 as determined by IEF as described herein, a temperature optimum within the range of 50–70° C., a molecular weight of about 170 kDa, and/or a specific activity of above about 250 GALU/mg protein. 1 GALU is the unit of α-galactosidase strength which is further defined in the materials and methods section below.

It will be understood that the preferred DNA construct of the invention is one, in which the DNA sequence is as shown in the appended SEQ ID No. 1 or 2.

The DNA sequence of the DNA construct of the invention may be isolated by well-known methods. Thus, the DNA sequence may, for instance, be isolated by establishing a cDNA or genomic library from an organism expected to harbour the sequence, e.g. a cell of any of the origins mentioned above, and screening for positive clones by conventional procedures. Examples of such procedures are hybridization to oligonucleotide probes synthesized on the basis of the full or partial amino acid sequence of the *A. niger* α-galactosidase comprising the amino acid sequence shown in SEQ ID No. 3 in accordance with standard techniques (cf. Sambrook et al., 1989), and/or selection for clones expressing an appropriate biological activity as defined above, and/or selection for clones producing a protein which is reactive with an antibody raised against the *A. niger* α-galactosidase.

A preferred method of isolating a DNA construct of the invention from a cDNA or genomic library is by use of polymerase chain reaction (PCR) using degenerate oligonucleotide probes prepared on the basis of the amino acid sequence shown in SEQ ID No. 3. For instance, the PCR may be carried out using the techniques described in U.S. Pat. No. 4,683,202 or by R. K. Saiki et al. (1988).

Alternatively, the DNA sequence of the DNA construct of the invention may be prepared synthetically by established standard methods, e.g. the phosphoamidite method described by Beaucage and Caruthers (1981), or the method described by Matthes et al. (1984). According to the phosphoamidite method, oligonucleotides are synthesized, e.g. in an automatic DNA synthesizer, purified, annealed, ligated and cloned in appropriate vectors.

Finally, the DNA construct may be of mixed genomic and synthetic, mixed synthetic and CDNA or mixed genomic and CDNA origin prepared by ligating fragments of synthetic, genomic or CDNA origin (as appropriate), the fragments corresponding to various parts of the entire recombinant DNA molecule, in accordance with standard techniques.

As stated above, the DNA construct of the invention may also comprise a genetically modified DNA sequence. Such sequence may be prepared on the basis of a genomic or cDNA sequence of the invention, suitably modified at a site corresponding to the site(s) of the polypeptide at which it is desired to introduce amino acid substitutions, e.g. by site-directed mutagenesis using synthetic oligonucleotides encoding the desired amino acid sequence for homologous recombination in accordance with well-known procedures, or by use of random mutagenesis, e.g. through radiation or chemical treatment.

Examples of suitable modifications of the DNA sequence are nucleotide substitutions which do not give rise to another amino acid sequence of the polypeptide, but which may correspond to the codon usage of the host organism into which the recombinant DNA molecule is introduced (i.e. modifications which, when expressed, results in e.g. an α-galactosidase comprising the amino acid sequence shown in the appended SEQ ID No. 3), or nucleotide substitutions which do give rise to a different amino acid sequence and therefore, possibly, a different polypeptide structure without, however, impairing properties of the polypeptide such as enzymatic properties thereof. Other examples of possible modifications are insertion of one or more nucleotides into the sequence, addition of one or more nucleotides at either end of the sequence and deletion of one or more nucleotides at either end of or within the sequence.

The recombinant expression vector carrying the DNA construct of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid or a bacteriophage. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. For instance, examples of suitable promoters for directing the transcription of the DNA construct of the invention in a fungal host cell are the TAKA promoter and the triose phosphate isomerase promoter of *Aspergillus oryzae*, the amyloglysidase promoter and the glyceraldehyde-3-phosphate dehydronase promoter of *Aspergillus niger* and the cellobiohydrolase I promoter of *Trichoderme reseei*.

The expression vector of the invention may also comprise a suitable terminator operably connected to the DNA construct of the invention. The terminator is suitably derived from the same source as the promoter of choice.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B.subtilis* or *B.licheniformis*, or one which confers antibiotic resistance such as ampicillin, kanamycin, chloramphenicol or tetracyclin resistance.

While intracellular expression may be advantageous in some respects, e.g. when using certain bacteria as host cells, it is generally preferred that the expression is extracellular. In order to obtain extracellular expression, the expression vector should normally further comprise a DNA sequence encoding a preregion, i.e. a signal peptide, permitting secretion of the expressed α-galactosidase or a variant thereof into the culture medium.

The procedures used to ligate the DNA construct of the invention, the promoter, terminator and other elements, respectively, and to insert them into suitable vectors containing the information necessary for replication, are well known to persons skilled in the art (cf., for instance, Sambrook et al. (1989)).

The cell of the invention either comprising a DNA construct or an expression vector of the invention as defined above is advantageously used as a host cell in the recombinant production of a polypeptide of the invention. The cell may be transformed with the DNA construct of the invention, conveniently by integrating the DNA construct in the host chromosome. This integration is generally considered to be an advantage as the DNA sequence is more likely to be stably maintained in the cell. Integration of the DNA constructs into the host chromosome may be performed according to conventional methods, e.g. by homologous recombination. Alternatively, the cell may be transformed with an expression vector as described below in connection with the different types of host cells.

The cell of the invention may be a cell of a higher organism such as a mammal or an insect, but is preferably a microbial cell, e.g. a bacterial or a fungal (including yeast) cell which, on cultivation, produces large amounts of the polypeptide.

Examples of suitable bacteria are grampositive bacteria such as *Bacillus subtilis, Bacillus licheniformis, Bacillus lentus, Bacillus brevis, Bacillus stearothermophilus, Bacillus alkalophilus, Bacillus amyloliauefaciens, Bacillus coagulans, Bacillus circulans, Bacillus lautus, Bacillus thuringiensis* or *Streptomyces lividans, Streptomyces murinus*, or gramnegative bacteria such as *E.coli*. The transformation of the bacteria may for instance be effected by protoplast transformation or by using competent cells in a manner known per se.

The yeast organism may favourably be selected from a species of Saccharomyces or Schizosaccharomyces, e.g. *Saccharomyces cerevisiae*. The filamentous fungus may advantageously belong to a species of Aspergillus, e.g. *Aspergillus orvzae* or *Aspergillus niger*. Fungal cells may be transformed by a process involving protoplast formation and transformation of the protoplasts followed by regeneration of the cell wall in a manner known per se. The use of Aspergillus as a host organism is described in, e.g., EP 238 023.

In a yet further aspect, the present invention relates to a method of producing a polypeptide of the invention, which method comprises cultivating a host cell as described above under conditions conducive to the production of the polypeptide and recovering the polypeptide from the cells and/or culture medium.

The medium used to cultivate the cells may be any conventional medium suitable for growing the host cell in question. Suitable media are available from commercial suppliers or may be prepared according to published recipes (e.g. in catalogues of the American Type Culture Collection).

The polypeptide may be recovered from the medium by conventional procedures including separating the cells from the medium by centrifugation or filtration, if necessary after disruption of the cells, precipitating the proteinaceous components of the supernatant or filtrate by means of a salt, e.g. ammonium sulphate, followed by purification by a variety of chromatographic procedures, e.g. ion exchange chromatography, affinity chromatography, or the like, the actual recovery method being dependant on the kind of polypeptide in question as well as the desired final purity thereof.

Depending on the degree of purification of the polypeptide produced by the process of the invention, the resulting polypeptide preparation may contain minor amounts of other enzymatic components inherently produced by the host cell used for the production. For instance, when a fungal cell, such as one of the genus Aspergillus, is used as a host cell for the production of a recombinant fungal α-galactosidase enzyme, certain of the enzymatic side-activities normally found in α-galactosidase preparations produced by conventional fermentation of a parent fungal strain may also be produced and recovered together with the recombinant polypeptide produced in accordance with the present invention. An example of an enzyme normally found in α-galactosidase preparations prepared by conventional techniques is the enzyme invertase. This enzyme is inherently produced by a number of Aspergillus strains and consequently may also be found in α-galactosidase preparations produced by Aspergillus strains in accordance with the present invention, although in a considerably lower amount as compared to the α-galactosidase than what is observed in conventional fermentation. Thus, in the context of the present invention, a substantial increase in the ratio of α-galactosidase to other enzymatic activities may be obtained in addition to the increased total yield of α-galactosidase.

If it is desired to produce substantially pure α-galactosidase or alternatively α-galactosidase preparation free from certain undesired enzymatic side-activities (an example of which—for some uses of the α-galactosidase—is invertase) one may either remove the side-activity(ies) by purification or one may choose a production organism incapable of producing the side-activity(ies) in question.

The α-galactosidase encoded by the DNA construct of the invention may be used for a number of purposes involving hydrolysis of α-galactosides to galactoses and sucroses.

For instance the α-galactosidase preparation encoded by the DNA construct and produced by the process of the invention may be used for the hydrolysis of α-galactosides present in, e.g., plants or plant parts which, for instance, are intended for nutrition of mammals or for fermentation of microorganisms. As indicated above, such plants and plant parts comprise legumes such as peas and beans, nuts, seeds, grains, cereals and vegetables including potatoes, beets and chicory, as well as processed products thereof including flour, meal, bran, molasses, etc. Thus, the α-galactosidase enzyme prepared according to the invention may be used for the pre-treatment of food or feed containing α-galactosides and for modification of soy bean or sugar beet molasses used as a substrate in the fermentation of microorganisms.

One important use of the α-galactosidase preparation prepared according to the invention is in the modification of soy beans or soy products such as soy bean molasses, soy bean sauce, soy bean milk, and soy bean whey.

Accordingly, in a further aspect the present invention relates to a method of preparing an enzyme-modified soy bean product comprising subjecting a composition containing the soy bean product to be modified to enzymatic treatment in the presence of an α-galactosidase preparation produced according to the invention. The enzymatic treatment may be performed by use of methods known in the art. For instance, soy bean meal may be modified by suspending the soy bean product in water so as to obtain a dry matter content in the resulting suspension of about 15–20%, adjusting pH to about 4.5–6 and treating the resulting suspension with 0.5% of an α-galactosidase preparation of the invention comprising about 500 GALU/g for 2–8 hours at 50° C. The resulting modified product may subsequently be spraydried. Furthermore, soy bean products may be produced as described by Olsen et al., 1981 and Eriksen, 1983, and the α-galactosidase preparation may be added, when appropriate, during the production. In the preparation of soy milk the α-galactosidase preparations may be added to the extract resulting after separation of solid particles from the soy bean material or during evaporation or in the final concentrated soy milk product.

Alternatively, a soy bean product may be treated by a method comprising
 a) inserting a DNA construct of the invention encoding an α-galactosidase, optionally present in a suitable expression vector, into a suitable host organism,
 b) culturing the host organism in a suitable culture medium under conditions permitting expression of the polypeptide encoded by the DNA construct, and recovering the resulting polypeptide from the culture, and
 c) subjecting a composition containing the soy bean product to be modified to enzymatic treatment in the presence of the polypeptide recovered in step b).

Step a) and b) may be performed as disclosed herein.

The α-galactosidase preparation produced according to the invention may further be used for the production of sugar from sugar beets in accordance with well-known procedures to improve the sugar yield by hydrolysing raffinose and stacchyose to galactose or sucrose.

Another important use of the α-galactosidase prepared according to the invention is for the in vivo conversion of α-galactoside-linked sugars in mammals, e.g. as described in WO 90/14101.

The α-galactosidase preparation may thus be used as digestive aid. For this purpose the α-galactosidase preparation may be combined with a suitable carrier or excipient so as to be in the form of a tablet, a capsule, a powder, a liquid, or in a soft-gel capsule form. The amount of α-galactosidase present in such formulations is in the range of 500–20000 GALU/G.

In a further aspect the present invention relates to a food or feed comprising an α-galactosidase preparation prepared according to the invention. The α-galactosidase preparation is typically included in an amount corresponding to about 1–20 GALU/g of food or feed. Examples of food or feed in which the α-galactosidase preparation may be included is given above.

Figure 2:
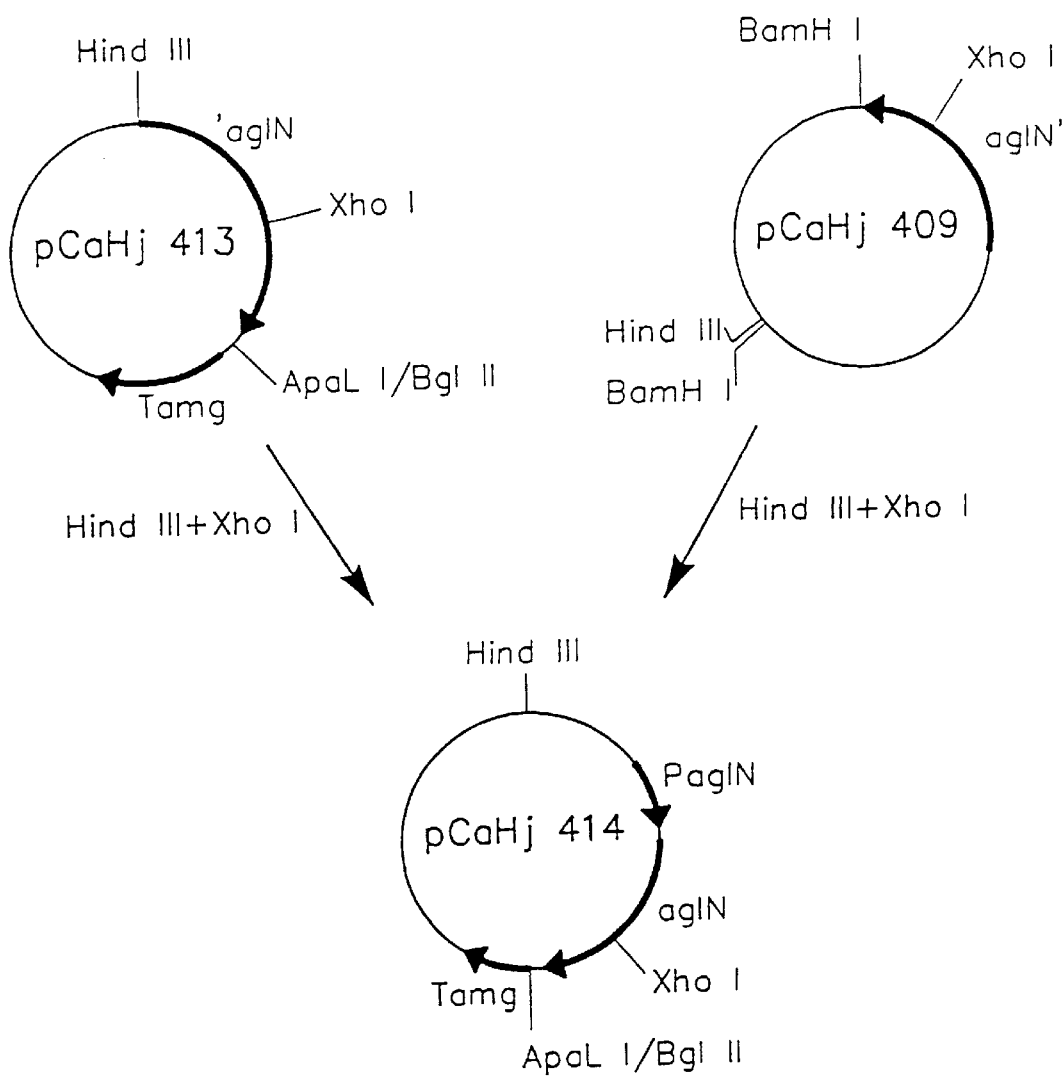
Figure 3:
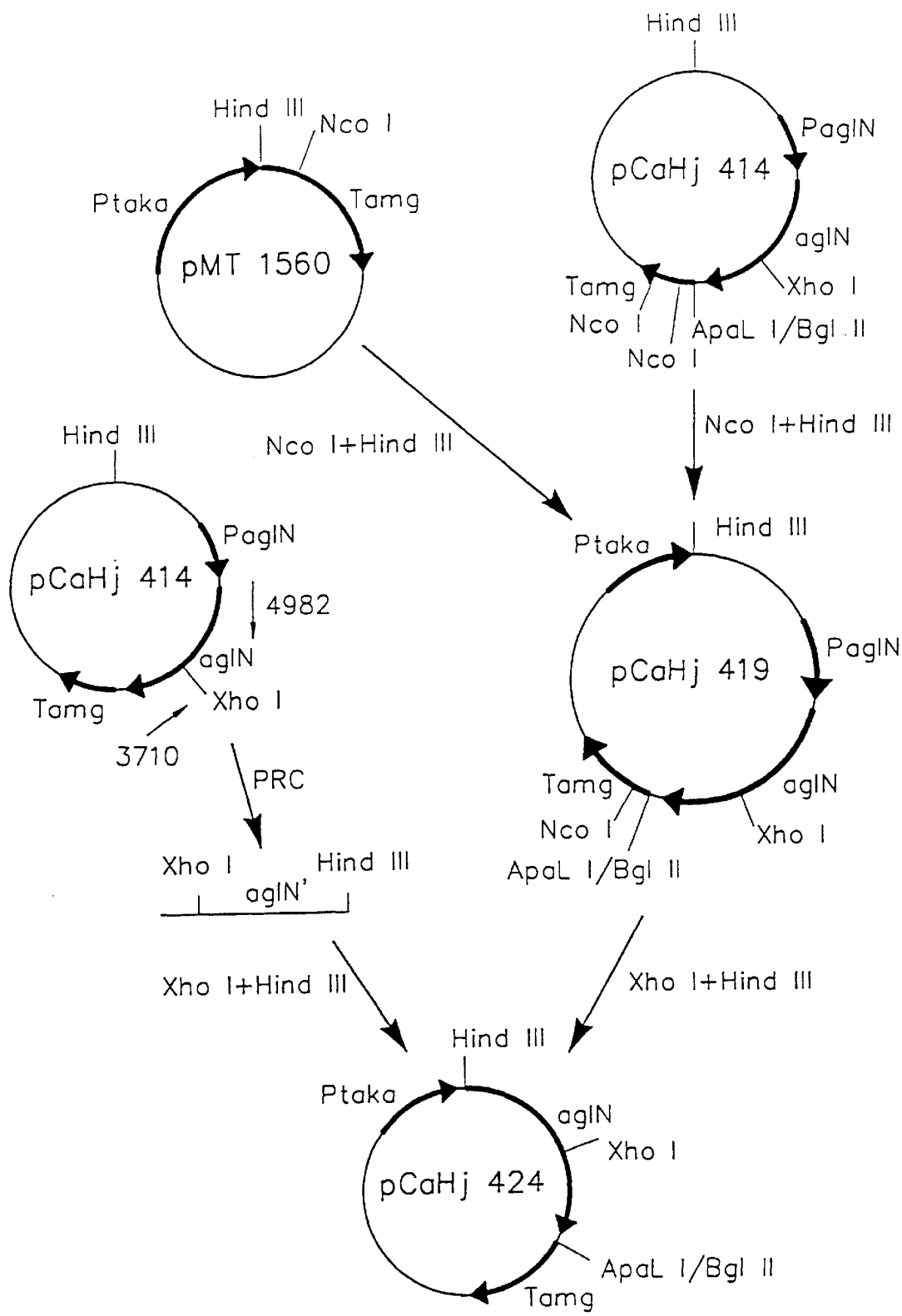
Figure 4:
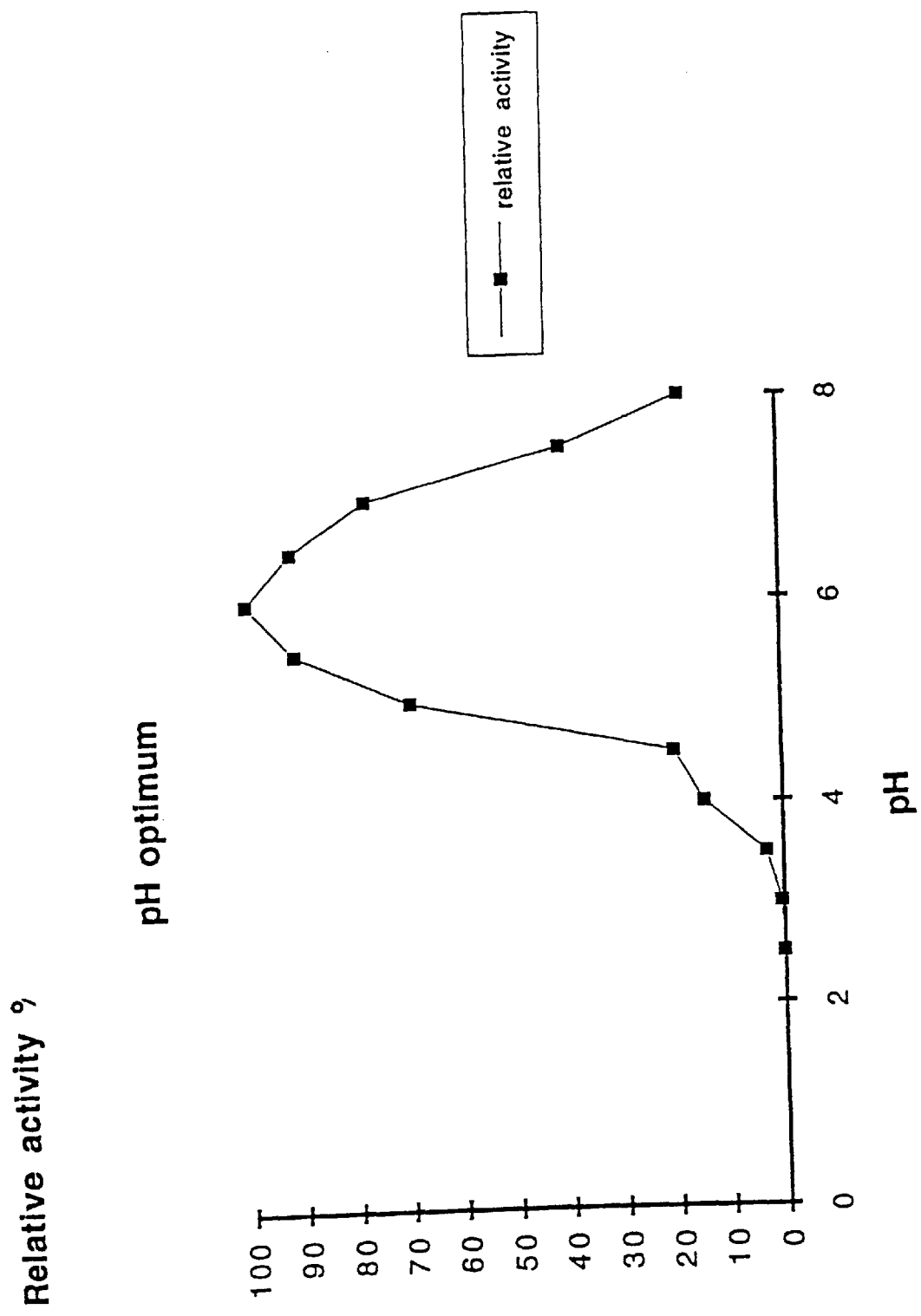
Figure 5:
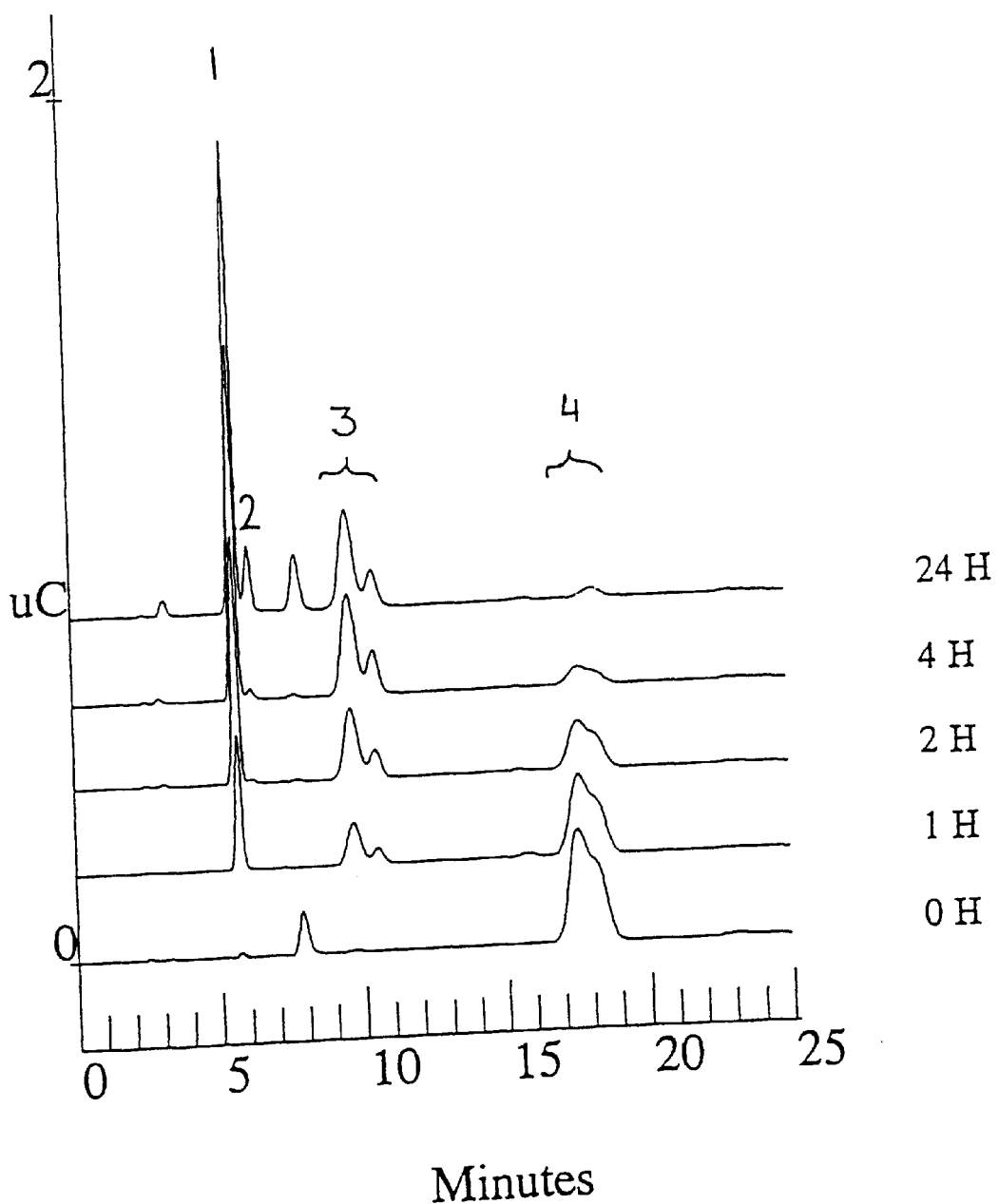
Figure 6:
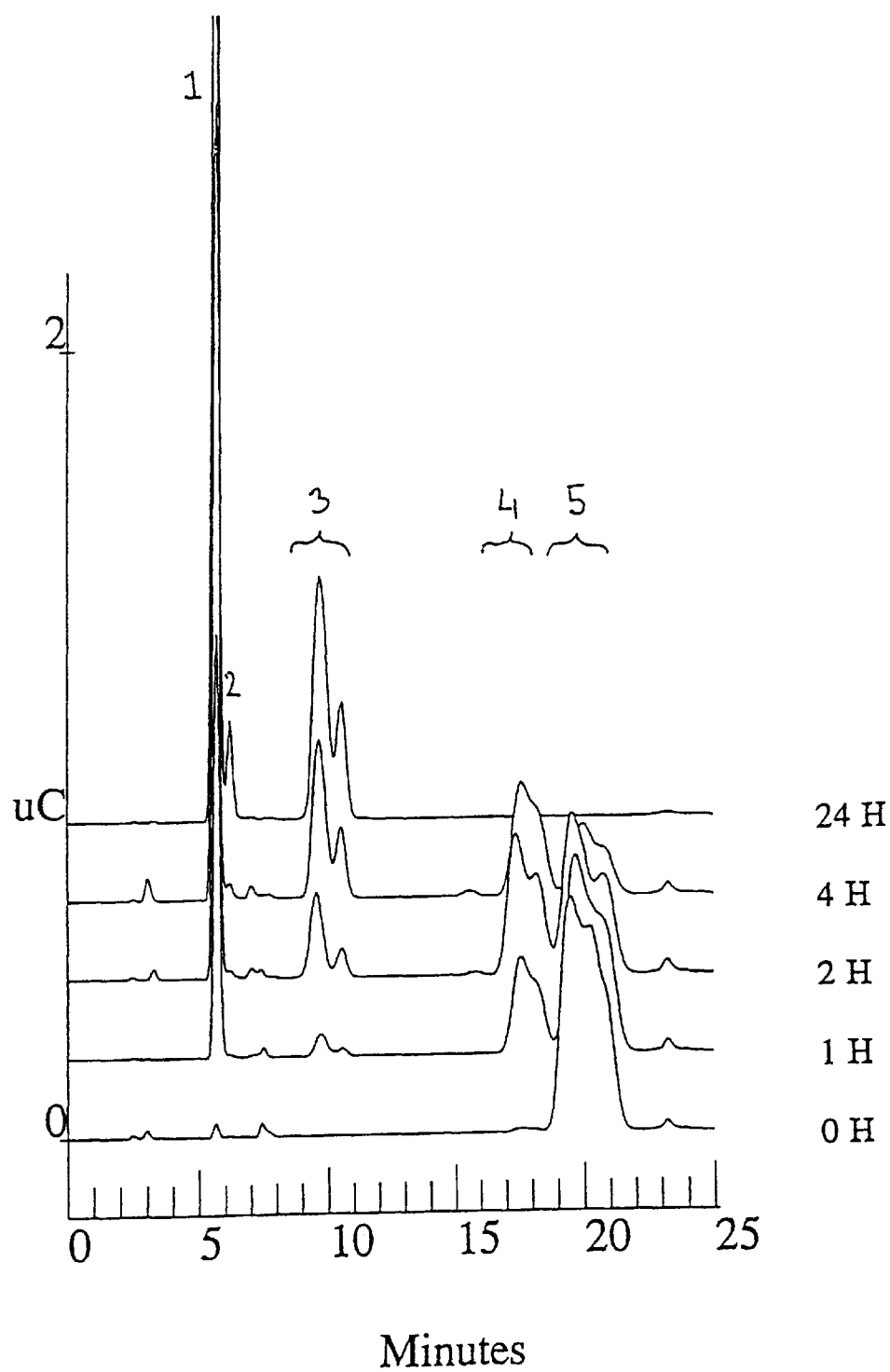

The present invention is described in the following by reference to the appended drawings, in which FIG. 1 illustrates the construction of pCaHj 413 as described in Example 4, FIG. 2 illustrates the construction of pCaHj 414 as described in Example 4, FIG. 3 illustrates the construction of pCaHj 424 as described in Example 4, FIG. 4 illustrates the pH optimum of α-galactosidase, FIG. 5 is a HPLC chromatogram illustrating the degradation of raffinose by α-galactosidase, and FIG. 6 is a HPLC chromatogram illustrating the degradation of stacchyose by α-galactosidase.

The present invention is further illustrated in the following examples, which are not, in any manner, intended to limit the invention as disclosed herein.

MATERIALS AND METHODS

Starting material

The α-galactosidase preparation used in the following examples is a commercial *A. niger* α-galactosidase preparation (Alpha-Gal™, Batch KAN 0001) available from Novo Nordisk A/S, Denmark.

Determination of α-Galactosidase Activity (GALU)

1 GALU is defined as the amount of α-galactosidase required for hydrolyzing 1 μmole p-nitrophenyl α-D-galactopyranoside (to p-nitro phenol+galactose) in one minute under the following conditions:

Substrate: 0.80 mM p-NPGal
pH: 5.5—acetate buffer 0.0333M
Temperature: 37° C.
Reaction time: 15 min.
Reagents
1. BUFFER: Acetate buffer 0.05 M, pH 5.5
2. SUBSTRATE: 1.2 mM p-Nitrophenyl-α-D-galactopyranoside
3. STOP REAGENT: Borax—NaOH buffer 0.0625 M, pH 9.7
4. COLOUR STANDARD: 4-Nitrophenol, 240 μM Procedure A standard curve is prepared by mixing 2 ml of substrate and 1 ml of various dilutions of colour standard (prepared with demineralized water) and adding 5 ml of stop reagent. When making the colour standard blank use demineralized water instead of colour standard. Measure $OD_{405}$.

Weigh and dilute the enzyme preparation to a concentration corresponding to an activity of about 0.0015 GALU/ml.

|  | Sample | Sample blank |
|---|---|---|
| Sample | 1 ml | 1 ml |
| Preheat substrate for 5 minutes | 37° C. | |
| Add substrate (stop watch) and mix | 2 ml | |
| Incubation for 15 minutes | 37° C. | room temp. |
| Add stop reagent and mix | 5 ml | 5 ml |
| Substrate - room temperature | | 2 ml |
| Measure $OD_{405}$ within 30 minutes | | |

Calculation of Activity

Make the colour standard curve (▲OD against concentration). The activity is calculated according to the following formula:

$$Act = \frac{(A_S - A_B) \cdot F_S \cdot 10^{-3}}{T \cdot M}$$

where
 $A_S$=The reading on the standard curve in μM 4-NP, corresponding to $OD_{405}$ for the sample.
 $A_B$=The reading on the standard curve in μM 4-NP, corresponding to $OD_{405}$ for the sample blank.
 $F_S$=Dilution factor for the sample.
 T=Reaction time in minutes (=15).
 M=Amount of sample weighed out.
 $10^{-3}$=Conversion factor 1 ml.

Fed batch fermentation

Fed batch fermentation was performed in a medium comprising maltodextrin as a carbon source, urea as a nitrogen source and yeast extract. The fed batch fermentation was performed by innoculating a shake flask culture of *A. oryzae* host cells in question into a medium comprising 3.5% of the carbon source and 0.5% of the nitrogen source. After 24 hours of cultivation at pH 7.0 and 34° C. the continuous supply of additional carbon and nitrogen sources were initiated. The carbon source was kept as the limiting factor and it was secured that oxygen was present in excess. The fed batch cultivation was continued for 4 days, after which the enzyme could be recovered by centrifugation, ultrafiltration, clear filtration and germ filtration.

Characterization of an enzyme of the invention pH optimum is measured by using 2 mM PNP-α-galactosidase in 0.1 M citrate/phosphate buffers pH 2.5–10 as a substrate. To 0.5 ml substrate is added 10 μl enzyme solution (100×diluted in 3 mg/ml BSA), the mixture is incubated at 30° C. for 15 minutes and the enzyme is heat-inactivated at 95° C. Three samples and one blank are prepared. 100 μl are pipetted into a microtiter plate well, 100 μl 1M tris buffer pH 7.0 are added and the absorbance is measured in the microtiter reader at 405 nm. Paranitrophenol is used as a standard. The specific activity at the optimal pH is calculated.

Temperature stability is measured by leaving the enzyme solution (in BSA or in 0.25% raffinose) at different temperatures for 1 and 2 hours before incubations are carried out at optimal pH in PNP-α-galactoside. Measurements are carried out as above.

Specific activity towards raffinose is measured by carrying out incubations at optimal pH at different raffinose concentrations (2–32 mM). Released galactose is determined by the amount of reducing sugars.

Reducing sugars are determined by reaction, in microtiter plates, with a PHBAH reagent comprising 0.15 g of para hydroxy benzoic acid hydrazide (Sigma H-9882), 0.50 g of potassium-sodium tartrate (Merck 8087) and 2% NaOH solution up to 10.0 ml. Results of blanks are subtracted.

In order to test for activity towards raffinose and stacchyose with and without the presence of galactose and sucrose, solutions are mixed according to the table below. The buffer is 0.1 M acetate buffer at the optimal pH for each enzyme. 10 μl of enzyme solution (diluted 10 times) is added and incubations are carried out at 30° C. for 0, 1, 2, 4 and 24 hours. 25 μl of the supernatant is analysed on the Dionex HPLC system (PA1 column, 0.12 M NaOH eluent, 1 ml/min flow rate, Pulsed Amperometric Detection) which separates all the saccharides. This experiment should also reveal if any transferase activity can be ascribed to the α-galactosidases.

Experiment

|   | raff. 1% | stach. 4% μl | sucr. 10% μl | gal. % μl | buffer μl |
|---|---|---|---|---|---|
| 1. | 200 |     |     |     | 800 |
| 2. |     | 200 |     |     | 800 |
| 3. |     |     | 200 |     | 800 |
| 4. | 200 |     |     | 200 | 600 |
| 5. |     | 200 |     | 200 | 600 |
| 6. |     |     | 200 | 200 | 600 |
| 7. | 200 | 200 | 200 |     | 400 |

EXAMPLE 1

Purification and characterization of α-galactosidase from *Aspergillus niger*

Salt precipitation

A sample of the α-galactosidase preparation was washed with 5 volumes of ionwater in an Amicon-UF-cell (membrane GR 60PP, Cut Off 25.000). Salt precipitation was achieved by use of $(NH_4)_2SO_4$ at 60% saturation (385 g/l), at which degree of saturation α-galactosidase had been shown to precipitate. The $(NH_4)_2SO_4$ was added slowly (more than one hour) under stirring at room temperature. The pH was kept constant at pH 5.5 by addition of a base.

The precipitate was redissolved in water and washed in an Amicon-UF-cell (membrane GR 60 PP) until a conductance of about 0.9 mS was reached.

Ionexchange

The redissolved and washed precipitate was subjected to anionexchange on a DEAE-Sepharose-CL-6B column equilibrated with a citrate/phosphate buffer, pH 5.5 (0.002 M citric acid/0.006 M $Na_2HPO_4$), and a conductivity of about 0.9 mS. The α-galactosidase was eluted with 0–0.5 M NaCl and fractions containing α-galactosidase activity were pooled.

Gelfiltration

The pooled α-galactosidase fractions were concentrated 10 x to obtain a protein content of about 16 mg/ml. The gelfiltration was performed on a Sephadex G100 (Mw 4.000-150-000) gelfiltration column equilibrated with the buffer specified above.

The α-galactosidase which was present in the front fraction and contained 5.6 mg of protein, was subsequently analysed for purity by use of the IEF Phast system and the SDS-PAGE Phast system as described below.

The specific activity of the front fraction was determed to 264 GALU/mg Protein as described above. The protein content was determined spectrophotometrically at 280 nm.

IEF

The α-galactosidase fraction was run on an IEF-PAA pH 4–6.5 (Pharmacia Phast System File Nos. 100 and 200). A strong bond could be observed at pH 4.3 and a weak shadow was observed at pH 4.2. It was concluded that the pI of the purified enzyme was 4.3.

SDS-PAGE

The α-galactosidase fraction was run on a SDS-gradient gel PAA 10–15 (Pharmacia Phast System as above). Before the sample was loaded the protein was subjected to denaturation and reduction by boiling and addition of DTT (1,4-Dithio-DL-threitol). A strong bond was observed at Mw 90.000 and a shadow at Mw 100.000. When no boiling with DTT was performed the SDS-analysis resulted in a bond at Mw 170.000 indicating the molecular weight of the intact protein. The fact that the Mw of the intact protein is 170.000 is in accordance with the fact that the α-galactosidase was contained in the front fraction obtained from the gelfiltration analysis, in that the Mw of proteins contained in the front fraction would be expected to be higher than 150.000.

It can thus be concluded that the α-galactosidase enzyme from *A. niger* described herein is a dimer of two protein chains each having a molecular weight of about 90.000.

EXAMPLE 2

Preparation and characterization of α-galactosidase peptides

Chemical degradation of a purified α-galactosidase preparation with surplus CNBr was carried out in 70% HCOOH for 24 h at 25° C. Enzymatic degradation using chymotrypsin was carried out in 0.05 M $NH_4HCO_3$, 2 M urea for 5 h at 37° C. at an enzyme: substrate ratio of 1:40 (w:w) Peptides were purified using microbore reversed phase HPLC employing either C4 or C18 columns eluted with linear gradients of 75% aqueous 2-propanol in 0.1% aqueous TFA (triflouroacetic acid). Purified peptides were sequenced using an Applied Biosystems 473A protein sequencer.

The following two peptides were obtained from chemical degradation with CNBr:

CNBr-peptide 1

Gly-Ala-His-Leu-Ser-Ala-Val-Pro-Asn-Ala-Gln-Thr-Gly-Arg-Thr-Val-Pro-Ile-Thr-Phe-Arg-Ala-His-Val- (SEQ ID No. 4)

CNBr-peptide 2

Asp-Asp-Gly-Trp-Phe-Gly-Asp-Lys-Tyr-Pro-Arg-Val-Ser-Asp-Asn-Ala-Gly-Leu-Gly-Asp-Asp- (SEQ ID No. 5)

The following peptides were obtained from the enzymatic degradation using chymotrypsin:

Chymotrypsin-peptide 1

Thr-Thr-Arg-Phe-Pro-Asp-Val-Leu-Trp (SEQ ID No. 6)

Chymotrypsin-peptide 2

Thr-Ser-Asp-Asn-Thr-Asp-Ala-Ile-Asp-Arg-Ile-Thr-Ile-Gln-Phe (SEQ ID No. 7)

Chymotrypsin-peptide 3

Arg-Leu-Arg-Leu-Pro-Gln-Asp-Ser-Gln-Trp-Pro-Ala-Ala-Leu-Phe (SEQ ID No. 8)

Chymotrypsin-peptide 4

Gly-Leu-Glu-Leu-Asp-Pro-Ala-Thr-Val-Glu-Gly-Asp-Glu-Ile-Val-Pro-Glu-Leu (SEQ ID No. 9)

Chymotrypsin-peptide 5

Val-Met-Asp-Asp-Gly-Trp-Phe-Gly-Asp-Lys-Tyr-Pro-Arg-Val-Ser-Asp-Asn-Ala-Gly- (SEQ ID No. 10)

It may be noted that amino acid residues 3–19 of the chymotrypsin-peptide 5 are present in CNBr-peptide 2 (amino acid residues 1–17).

EXAMPLE 3

Cloning of an *Aspergillus niger* α-galactosidase

Generation of an α-galactosidase probe

As noted in Example 2 above chymotrypsin-peptide 5 and CNBr-peptide 2 are overlapping. Together they reveal the peptide:

VMDDGWFGDKYPRVSDNAGLGDD (SEQ ID No. 11)

Polymerase chain reaction (PCR) primers were designed in order to amplify the DNA sequence encoding this peptide sequence.

In the 5' end (sense strand) the following degenerate primer was used:

5' TTACTAGTNATGGAYGAYGGNTGGTT 3' (5'#1: 64 species) (SEQ ID No. 12).

A Spe I site (ACTAGT) was anchored in the 5' end of this primer.

In the 3' end (sense strand) the following degenerate primers were used:

5' TTGAGCTCRTCNCCYAANCCNGCRTT 3' (3'#1: 512 species) (SEQ ID No. 13).

5' TTGAGCTCRTCNCCNAGNCCNGCGTT 3' (3'#2: 512 species) (SEQ ID No. 14) 5' TTGAGCTCRTCNC-CNAGNCCNGCATT 3' (3'#3: 512 species) (SEQ ID No. 15)

5'#1 was used together with either 3'#1, 3'#2 or 3'#3.

Genomic DNA was prepared from *A. niger* (ATCC 16882) as described by Leach et. al., 1986.

This DNA was used as template in the PCR reactions (0.05 μg genomic DNA, 100 pmol of each degenerate primer, 200 μM of dATP, dCTP, dGTP and dTTP, 1.5 mM MgCl$_2$, 50 mM KCl, 0.01% gelatine, 10 mM Tris-HCl pH 8.3 in a total volume of 100 μl), and the following PCR program was run:

94° C. for 2 min., 1 cycle (0.5 μl of amplitaq' taq polymerase (Perkin Elmer - Cetus) was added during this incubation).

94° C. for 1 min., 50° C. for 1 min., 72° C. for 2 min., 30 cycles.

72° C. for 5 min., 1 cycle.

The products of the PCR amplifications were concentrated and run on an agarose gel. In the amplifications employing 3'#1 and 3'#3 no product except for 'primer dimer' was seen, but in the amplification employing 3'#2 a distinct fragment of approx. 80 bp. was seen. This fragment was isolated, digested with the restriction enzymes SpeI and SacI and ligated to the vector pUC19 (Yanish-Perron et al., 1985) digested with XbaI and SacI. The ligation mixture was transformed into *Escherichia coli* MC 1000 (Casadaban et al., 1980) made r$^-$m$^+$ by conventional methods.

Plasmid DNA isolated from a transformant was sequenced using the Sequenase kit (United States Biochemicals) following the manufacturers instructions. The sequence showed that the cloned PCR fragment actually encoded the peptide fragment described above. The insert (86bp) of this plasmid was used as a probe in order to clone the α-galactosidase gene.

Labelling of the probe

A radioactive labelled probe was prepared in the following way: 5 μg of the plasmid was digested with EcoRI and SalI and the 86 bp fragment was isolated from an agarose gel and dissolved in 20 μl water. This was used as a template in a PCR reaction including 2 μl of the fragment, 50 pmol primer 5'#1, 50 pmol primer 3'#2, 10 pmol α$^{32}$PdATP (3000 Ci/mmol) (DuPont NEG-012H), 10 pmol dTTP, 10 pmol dCTP, 10 pmol dGTP, 1.5 mM MgCl$_2$, 50 mM KCl, 0.01% gelatine, 10 mM Tris-HCl pH 8.3 in a total volume of 100 μl.

The following temperature cycling program was run:

94° C. for 2 min., 1 cycle (0.5 μl of amplitaq' taq polymerase (Perkin Elmer - Cetus) was added during this incubation).

94° C. for 1 min., 50° C. for 1 min., 72° C for 2 min., 30 cycles.

72° C. for 5 min., 1 cycle.

The labelled fragment was isolated using a Sephadex G50 spun column as described by Maniatis et. al. (Maniatis et al., 1982). The probe was heat denatured for 5 min, 100° C., and then added to the hybridization mixture.

Genome cloning of the α-galactosidase

Genomic DNA from *A. niger* was prepared as described above, and digested with various restriction enzymes, and the digestions were used for Southern blot analysis using the described α-galactosidase probe.

A 4.5 kb BamHI fragment hybridized to the probe. This fragment was cloned the in the following way:

*A. niger* genomic DNA was digested with BamHI, and fragments of 4–5 kb were isolated from an agarose gel. The fragments were ligated to pUC19 digested with BamHI and dephosphorylated with calf intestine alcaline phosphatase. The ligation mixture used to transform *E. coli* using ampicillin selection. 5000 clones were screened for the 4.5 kb α-galactosidase fragment by colony hybridization using the described α-galactosidase probe, and hybridizing clones were selected.

Sequence analysis using the primers 3710 and 3711 of plasmid DNA isolated from one of these clones confirmed that the cloned fragment contained an α-galactosidase encoding sequence. This plasmid was termed pCaHj409. Sequence deduced from the M13 universal primer (United States Biochemicals) revealed that the 3' end of the gene was missing.

2178 bp of the insert covering the cloned part of the α-galactosidase gene was sequenced from both strands using various primers.

3710 5' GCGTTATCGGACACTCG 3' (SEQ ID No. 16)

3711 5' GTTTGGGGACAAGTACC 3' (SEQ ID No. 17)

cDNA cloning by PCR mRNA was prepared by guanidinium thiocyanate extraction followed by centrifugation in cesium chloride solution as described by Sambrook et. al, 1989, using fresh mycelium.

First strand cDNA was synthesized from an oligo dT primer using the BRL superscript cDNA kit following the manufacturers instructions.

The cDNA gene was cloned as a 5' fragment and a 3' fragment using the rapid amplification of cDNA ends (RACE) method as described by Frohman, 1990.

The primer 3710 was used as a sequence specific primer for amplification of the 5' end, and 3711 was used as a sequence specific primer for amplification of the 3' end. In both cases the primers 2010 and 4433 were used as hybrid oligo dT primer and adaptor primer, respectively.

2010 5' CTGCAGTCGACTCTAGAGGATCCGCGGC-CGCTTTTTTTTTTTTT TTTTTTTTTTTT 3' (SEQ ID No. 18)

4433 5' TTACTGCAGTCGACTCTAGAGGATCCGCG 3' (SEQ ID No. 19)

Composition of PCR reaction mixtures and the cycling profiles were as described by Frohman, op cit.

The obtained 430 bp 5' fragment was digested with BamHI and XhoI and ligated to pUC19 digested with BamHI and SalI. The ligation mixture was transformed into *E. coli* using ampicillin selection. A plasmid containing an insert was sequenced from both strands using various primers. The sequence confirmed that the fragment was an α-galactosidase cDNA fragment.

The obtained 1300 bp 3' fragment was digested with XhoI and XbaI and ligated to pUC 19 digested with Sal I and Xba I. The ligation mixture was transformed into *E. coli* using ampicillin selection. A 1300 bp insert from a plasmid was confirmed to be an α-galactosidase fragment by sequence analysis from both strands using various primers. This plasmid was termed pCaHj 410.

The genomic sequence and the cDNA sequence are shown in SEQ ID Nos. 1 and 2, respectively. The nucleotide fragments 302–371, 628–716, 978–1032 of the genomic sequence represent intron sequences.

The α-galactosidase protein sequence showed about 30% homology to the *E. coli* α-galactosidase encoded by the gene rafA (Aslandis et al., 1989).

EXAMPLE 4

Expression of the α-galactosidase

Construction of α-galactosidase expression vectors

The plasmid pCaHj 409 was digested with Sal I and Pst I, and a 1.5 kb fragment was isolated and ligated to pUC 19 digested with Sal I and Pst I. After transformation into *E. coli* and isolation of plasmid, the resulting plasmid was digested with Sal I and EcoR I, and the 4.2 kb fragment was isolated. pCaHj 410 was digested with EcoR I and Sal I, and the 0.8 kb fragment was isolated and inserted into to the 4.2 kb fragment described above. The resulting plasmid was termed pCaHj 412. This plasmid was digested with ApaL I, the 3' recessed ends were filled in using the Klenow polymerase, and after phenol/chloroform extraction the mixture was digested with Hind III. The resulting 2.2 kb fragment was isolated.

The Aspergillus expression plasmid pToC 68 (described in WO 91/17243) was digested with Bgl II, the 3' recessed ends were filled in using the Klenow polymerase, and after phenol/chloroform extraction the mixture was digested with Hind III. The 4.6 kb fragment was isolated and ligated to the 2.2 kb fragment described above. The resulting plasmid, termed pCaHj 413, contained a part of the aglN gene fused to the terminator of the amyloglycosidase gene of *A. niger* (Tamg). The construction of pCaHj 413 is summarized in FIG. 1.

pCaHj 413 was digested with Hind III and Xho I, and the 4.1 kb fragment was isolated. pCaHj 409 was digested with Hind III and Xho I, and the 4.0 kb fragment containing the 5' end of the aglN gene was isolated and ligated to the pCaHj 413 fragment. The resulting expression plasmid, termed pCaHj 414, contained the aglN promotor followed by the aglN gene fused to the AMG terminator. The construction of pCaHj 414 is summarized in FIG. 2.

pMT 1560 (4169 bp) was derived from pHD 414 (described in WO 92/16634) by replacing the 617 bp BamH I—EcoR I fragment of pHD 414 with the BamH I—EcoR I digested PCR fragment obtained from a PCR reaction using pHD 414 as a template and the primers:

5'GCTCCTCATGGTGGATCCCCAGTTGTG-TATATAGAGGATTGAGGAAGGAA-GAGAAGTGTGGATAGAGGTAAATTGAGT-TGGAAACTCCAAGCATGGCATCCCTTGC 3' 106 mer (SEQ ID No. 20), and 5'TGTTCTGGCTGTGGTGTACAGG 3'22 mer (SEQ ID No. 21).

pMT 1560 was digested with Nco I and Hind III, and the 3.9 kb fragment was isolated. pCaHj 414 was digested with Nco I and Hind III, and the 5.2 kb fragment containing the aglN gene was isolated and inserted into the 3.9 kb pMT 1560 fragment. The resulting plasmid was termed pCaHj 419. This plasmid was digested with Hind III and Xho I and the 5.2 kb containing the TAKA promotor of *A. oryzae* and the 3' end of the aglN gene fused to the AMG terminator was isolated.

pCaHj 414 was used as a PCR template together with the primers 3710 and 4982 (containing a Hind III site followed by the ATG start codon of the aglN gene):

3710 5' GCGTTATCGGACACTCG 3' (SEQ ID No. 16)

4982 5' GCAAGCTTTATCATCACCACCATGAT 3' (SEQ ID No. 22)

The PCR conditions were as described in Example 3 above (in "Generation of an α-galactosidase probe"). The PCR fragment was digested with Hind III and Xho I and inserted into the 5.2 kb pCaHj 419 fragment. The resulting expression plasmid was termed pCaHj 424 and contained the aglN gene fused to the TAKA promotor in the 5' end and to the AMG terminator in the 3' end. The construction of pCaHj 424 is summarized in FIG. 3.

Transformation of *A. oryzae*

The plasmid pCaHj 414 was transformed into *Aspergillus oryzae* IFO 4177 using selection on acetamide by cotransformation with pToC 90 as described in WO 91/17243.

By cultivation in shake flasks or in submerged tank fermentation of the cotransformants activity was accumulated in the broth.

pCaHj 424 was transformed into *A. oryzae* IFO 4177 using the same method. Cotransformants expressed significantly higher amounts of α-galactosidase than pCaHj 414 transformants.

Purification of α-galactosidase

The culture supernatant from fermentation of *Aspergillus oryzae* expressing the recombinant enzyme is centrifuged and filtered through a 0.2 μm filter to remove the mycelia. 35–50 ml of the filtered supernatant (30–60 mg α-galactosidase) are ultrafiltrated in a Filtron ultracette or Amicon ultrafiltration device with a 10 kDa membrane to achieve 10 fold concentration. This concentrate is diluted 100 times in 25 mM Tris pH 8.0 in two successive rounds of ultrafiltration in the same device. This ultrafiltrated sample is loaded at 1.5 ml/min on a Pharmacia HR16/20 Fast Flow Q Sepharose anion exchanger equilibrated in 25 mM Tris pH 8.0. After the sample has been applied, the column is washed with two column volumes 25 mM Tris pH 8.0, and bound proteins are eluted with a linear increasing NaCl gradient from 0 to 0.6 M Nacl in 25 mM Tris pH 8.0. α-galactosidase elutes at approximately 0.25–0.3 M NaCl, but the enzyme in this fraction is not completely pure (approximately 80% purity). Thus, the α-galactosidase containing fractions were concentrated by ultrafiltration in Amicon ultrafiltration device with a 10 kDa membrane to a volume of 4.5 ml and applied to a HR 26/60 Sephacryl S200 gelfiltration column in 0.25 M amonium acetate pH 5.5 at a constant flow of 1 ml/min. α-galactosidase is eluted as one distinct peak with a purity of approximately 90%. In order to achieve material purified to electrophoretic homogeneity, the α-galactosidase containing fractions are pooled, and ultrafiltrated into 10 mM sodium phosphate pH 6.8. The sample is applied onto a 8 ml BioRad HTP hydroxyl apatite column (10 mm internal diameter) at a constant flow rate of 1 ml/min. Bound enzymes are eluted by increasing the sodium phosphate concentration from 10 mM to 0.2 M over 40 min. α-galactosidase elutes at approximately 0.1 M sodium phosphate, and is more than 95% pure in this fraction.

EXAMPLE 5

Characterization of α-galactosidase

The following properties of the α-galactosidase expressed in and purified from *A. oryzae* were determined by the methods described in the Materials and Methods section above.

The results obtained can be summarized in the following table:

| | |
|---|---|
| MW | 95 kDa |
| pH-optimum | 6.0 |
| stability in water | very stable |
| temperature stability in BSA for 1 hour | <60° C. |
| temperature stability in presence of raffinose | <70° C. |
| specific activity towards (μmol/mg enzyme/min) | |
| a) PNP-α-galactosidase | 90 |
| b) raffinose | 145 (100) |
| c) stacchyose | (350) |
| d) guar gum | (0) |
| inhibition by galactose | No |
| transferase activity | No |

Results in brackets are calculated from the HPLC results.

pH optimum

The pH optimum which is seen in FIG. 4 shows that the enzyme is most active at pH 6 but retains some activity in the whole range from pH 4–8. This is surprising in that the enzyme isolated from *A. niger* has a pH optimum in the range of 4–6.

Degradation of stacchyose and raffinose and HPLC analysis

From the HPLC chromatograms in FIG. 5 and 6 it is seen that degradation of raffinose (peak 4) is completed within 24 hours the reaction products being sucrose (peak 39, galactose (peak 1) and small amounts of fructose (peak 2). The degradation of stacchyose results in the formation of raffinose (peak 4), sucrose (peak 39 and galactose (peak 1). After 24 hours all stacchyose and raffinose has been converted into sucrose, galactose and small amounts of fructose.

It was surprisingly found that the enzyme was not inhibited by galactose.

REFERENCES CITED IN THE SPECIFICATION

Leach et. al., 1986, Fungal gent. newsl., 33, 32–33.

Yanish-Perron et al., Gene 33, 103–119 (1985)

Casadaban et al., J. Mol. Biol., 138, 179–207 (1980)

Maniatis et al., Molecular cloning, A laboratory manual, Cold Spring Harbor laboratory 1982

Sambrook, E. F. Fritsch and T. Maniatis. (1989), Molecular cloning, a laboratory manual. 2. edition. Cold Spring Harbor Laboratory press)

M. A. Frohman (1990). RACE, rapid amplification of cDNA ends. in: M. A. Innis et. al. PCR protocols, A guide to methods and applications. Academic press).

Aslandis et al., 1989, Nucleotide sequences and operon structure of plasmid borne genes mediating uptake and utilization of raffinose in *Escherichia coli*. J. Bact. 171, 6753–6763

WO 90/14101 (AEK DEVELOPMENT CORPORATION, US)

U.S. Pat. No. 3,846,239 of Nov. 5, 1974 (MONSANTO COMPANY)

Worthington et al., "α-Galactosidase Activity of Fungi on Intestinal Gas-Forming Peanut Oligosaccharides", J.Agr-.Food Chem., Vol. 22, No. 6 (1974)

U.S. Pat. No. 4,431,737 of Feb. 14, 1984 (ANIC, S.p.A., IT)

Cruz and Park, (1982), "Production of Funggal α-Galactosidase and Its Application to the Hydrolysis of Galactooligosaccharides in Soybean Milk", J. of Food Science—1973, Vol. 47

Zapater et al. (1990), Preparative Biochemistry, 20 (3&4), pp. 263–296

Bahl and Agrawal (1969), "Glycosidases of *Aspergillus niger*", J. of Biol. Chem., Vol. 244 (11), pp. 2970–2978

Christakopoulos et al. (1990), Process Biochemistry International, pp. 210–212

Chun and Lee (1988), Korean J. Food Sci. Technol. Vol. 20 (1), pp. 79–84

Jung and Lee (1986), Korean J. Food Schi Technol., Vol. 18 (6), pp. 450–457

Lee and Wacek (1970), "Galactosidases from *Aspergillus niger*", Archives of Biochem. and Biophysics 138, pp. 264–271

Adya and Elbein (1976), J. of Bact., Vol. 129 (2), pp. 850–856

Kaneko et al. (1991), Agric. Biol. Chem. 55 (1), pp. 109–115

Rackis, J. J. (1975), ACS Symposium Series 15, "Physiological Effects of Food Carbohydrates", pp. 207–222

Bahl et al., "α-Galactosidase, β-Galactosidase, and β-N-Ace-tylglucosaminidase from *Aspergillus niger*" (1972), Methods in Enzymology, Vol 28, pp. 728–734

Overbeeke et al., 1990, Applied and Environmental Microbiology, Vol. 56, No. 5., pp. 1429–1434.

Lipman and Pearson, 1985, Science 227, p. 1435

Hudson et al, 1989, Practical Immunology, Third edition, Blackwell Scientific Publications.

Beaucage and Caruthers, 1984, Tetrahedron Letters 22, 1981, pp. 1859–1869

Matthes et al., 1984, The EMBO J. 3, 1984, pp. 801–805

R.K. Saiki et al., 1988, Science 239, pp. 487–491

Olsen and Adler-Nissen, Sonderdruck aus ZFL - Zeitschrift für Lebensmittel-Technologie und Verfahrenstechnik 31. Jahrgang 1980—Heft 8—(Teil I); 32. Jahrgang 1981—Heft 2—(Teil II)

Eriksen S., J. Food Sci. 48(2): 445–557, 1983.

What is claimed is:

1. An isolated polypeptide from Aspergillus having α-galactosidase activity that is not inhibited by galactose and characterized as having (a) a pH optimum in the range of 5.0–7.0;

(b) a temperature optimum within the range of 50–70° C.; and (c) a pI in the range of 4.0–5.5;

(d) a molecular weight of about 170,000 Da.

2. The isolated polypeptide of claim 1, further characterized as having (e) a specific activity of above about 250 GALU/mg protein.

3. The isolated polypeptide of claim 1, wherein the peptide is derived from *Aspergillus niger.*

4. An isolated polypeptide derived from a strain of Aspergillus having α-galactosidase activity that has pH optimum in the range of 5.0–7.0 and is not inhibited by galactose, wherein said polypeptide is encoded by a DNA sequence which hybridizes with the DNA sequence of SEQ ID NO:1 or SEQ ID NO:2 under the conditions of hybridization at 45° C. for 18 hrs, followed by repeated washing in 6×SSC, 0.1% SDS at 45° C.

5. The isolated polypeptide of claim 4, where the strain is *Aspergillus niger.*

6. The isolated polypeptide of claim 4, where the strain is *Aspergillus niger* ATCC 16882.

7. An isolated polypeptide having α-galactosidase activity, comprising:

(a) the amino acid sequence of SEQ ID NO:3; or (b) an amino acid sequence which has at least 90% identity to the sequence of SEQ ID NO:3.

8. The isolated polypeptide of claim 7, wherein the amino acid sequence has at least 95% identity to the amino acid sequence of SEQ ID NO:3.

9. An isolated polypeptide having α-galactosidase activity encoded by a DNA sequence selected from the group consisting of:

(a) a DNA sequence encoding amino acids 20–677 of the amino acid sequence of SEQ ID NO:3; and (b) the coding region of SEQ ID NO:1.

\* \* \* \* \*

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 2641 base pairs
      (B) TYPE: nucleic acid
      (C) STRANDEDNESS: single
      (D) TOPOLOGY: linear (ix) FEATURE:

(xi) SEQUENCE DESCRIPTION: SEQ ID NO:1:

```
GTAGTCCCAG CCACGTTGGG GAATGAGAAG TGGGGGTGCC AAGCCGGAGT GGGGGATGAT      60

GCCCAGCAAG AAACTGGATA CCCTCCGATG TTTCCCCGGA TGCAGTCGAG ACCGTCCGGG     120

GATAAAAGGC CGGTGAGAGG AAGAACTGCT GCTTCACTCA CCTGCCACAT GTGTTAGGAT     180

TGACGGCCAG CAATATCATC ACCACCATGA TCGGTCTTCC CATGCTGTGG TGCCTGGGCC     240

TTTTTACGTT ATACGGTCAT TCTGCAGACA CGCCCGCAAC TGGGGTTTCA AACCCACAGA     300

GTATGGACTG CCGGGGGGA GGATGCTACT GCAACGCTTG ATCTTCATTC GGAGTAAGCT     360

GACCAAACAG CGATCGTTAC GAATGGCACT AGTTTCCGAT TGAACGGCGA CAATGTCTCA     420

TATCGATTCC ATGTCAACAG TACCACCGGC GACTTGATTT CTGATCATTT TGGTGGTGTC     480

GTCTCCGGCA CAATCCCTTC GCCAGTGGAA CCTGCTGTCA ACGGCTGGGT CGGCATGCCT     540

GGTCGAATCC GCCGGGAGTT CCCCGACCAA GGCCGTGGGG ATTTCCGCAT CCCCGCCGTT     600

CGTATTCGGG AATCGGCAGG TTATACTGTT AGCGATCTCC ATATGTGTCG CACGAGGTGA     660

TCGAAGGTAA AAATGCTTTG CCCCGGCCTG CCTGCCACAT TTGGCGATGC GCAGGCTGTC     720

ACAACTTTGG TAGTCCATCT GTATGACAAC TATAGCTCCG TCGCGGCCGA CTTGTCATAC     780

TCCATATTTC CGAAATATGA TGCGATCGTG AGGAGTGTCA ATGTGATCAA CCAGGGCCCA     840

GGTAATATCA CTATCGAGGC CCTTGCAAGC ATAAGTATCG ATTTCCCCTA TGAAGACCTC     900

GACATGGTCA GCCTCCGAGG CGACTGGGCC AGAGAGGCAA ATGTTCAGAG AAGCAAAGTG     960

CAGTATGGCG TCCAGGGGTA AGTCAGCATA GCATAAAACC GACATGGTGA CCTTGCTGAC    1020

GGGAGAGTAG ATTCGGAAGC AGTACTGGAT ATTCCTCTCA CCTTCACAAT CCCTTCCTTG    1080

CCATAGTAGA TCCAGCTACT ACCGAATCGC AAGGCGAGGC ATGGGGTTTC AACCTTGTAT    1140

ATACCGGCTC TTTCTCGGCC CAAGTAGAGA AAGGATCGCA AGGTTTCACC CGGGCGCTGC    1200

TCGGCTTCAA CCCGGACCAA TTATCGTGGA ACCTTGGCCC TGGCGAGACT TTAACTTCCC    1260
```

-continued

```
CCGAGTGTGT TGCAGTCTAC TCGGACAAAG GCCTTGGCTC AGTGTCTCGC AAATTCCACC      1320

GGCTATATCG CAACCACCTC ATGAAGAGCA AGTTCGCCAC GTCCGACCGG CCGGTTCTGC      1380

TGAATAGCTG GGAAGGTGTT TATTTCGACT ACAATCAAAG CAGCATCGAA ACTCTTGCCG      1440

AAGAGTCCGC TGCCCTGGGT GTCCACCTCT TTGTCATGGA CGACGGCTGG TTTGGGACA       1500

AGTACCCTCG AGTGTCCGAT AACGCCGGAC TGGGCGACTG GATGCCCAAT CCAGCGCGCT     1560

TGCCGGACGG GTTGACCCCG GTCGTGCAAG ACATCACAAA TCTCACCGTC AATGGCACAG    1620

AGTCCACAAA ACTTCGCTTT GGTATTTGGG TGGAGCCCGA GATGGTCAAC CCCAATTCCA   1680

CTCTCTACCA CGAACACCCG GAGTGGGCGC TTCATGCCGG GCCTTACCCC CGTACCGAGC   1740

GTCGGAACCA GCTCGTCCTC AACCTGGCGC TTCCGGCTGT GCAGGACTTC ATCATAGACT   1800

TCATGACGAA CCTGTTACAA GATACCGGCA TTTCCTACGT CAAATGGGAC AACAACCGGG    1860

GAATACACGA GACGCCCTCT CCGTCGACTG ACCATCAGTA CATGCTTGGC CTCTACCGGG   1920

TGTTCGACAC ACTGACCACC CGCTTCCCGG ATGTCCTGTG GGAAGGATGT GCCTCGGGTG    1980

GAGGCCGCTT TGATGCTGGC ATGCTGCAGT ATGTCCCCCA GATCTGGACT TCCGATAACA   2040

CCGACGCCAT CGACCGAATC ACCATCCAAT TTGGGACCTC GCTTGCCTAC CCGCCATCAG   2100

CAATGGGTGC CCACCTCTCC GCGGTTCCTA ACGCACAGAC CGGTCGCACT GTGCCCATTA   2160

CTTTCCGCGC ACACGTTGCT ATGATGGGTG GTTCTTTCGG CTTGGAGCTG GATCCGGCGA    2220

CGGTGGAAGG GGACGAAATA GTTCCCGAGC TTCTTGCGCT GGCGGAAAAA GTGAACCCTA   2280

TCATTTTGAA CGGAGATCTG TATCGGCTAC GCCTACCTCA AGACTCCCAG TGGCCTGCCG   2340

CACTCTTTGT GACTCAGGAT GGCGCACAGG CTGTTCTGTT CTACTTCCAG GTGCCAGCCG   2400

AATGTCAACC ATGCCGTGCC GTGGGTCAGG CTGCAGGGGT TGGACCCTAA GGCGGACTAT   2460

ACCGTTGATG GAGATCAGAC GTATTCCGGG GCAACACTAA TGAATCTGGG GTTGCAGTAT   2520

AGTTTTGACA CCGAGTATGG TAGCAAGGTA GTTTTCCTGG AGAGGCAATG ATCGGAGAAA   2580

ATATCGCCAT GTATATACTC TCCGTGCCTT GTCAATGTGC AGATCTAGAG GGTGACTTAC   2640

A                                                                     2641
```

(2) INFORMATION FOR SEQ ID NO: 2:

(i) SEQUENCE CHARACTERISTICS:
        (A) LENGTH: 2034 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

```
ATGATCGGTC TTCCCATGCT GTGGTGCCTG GGCCTTTTTA CGTTATACGG TCATTCTGCA       60

GACACGCCCG CAACTGGGGT TTCAAACCCA CAGACGATCG TTACGAATGG CACTAGTTTC      120

CGATTGAACG GCGACAATGT CTCATATCGA TTCCATGTCA ACAGTACCAC CGGCGACTTG     180

ATTTCTGATC ATTTTGGTGG TGTCGTCTCC GGCACAATCC CTTCGCCAGT GGAACCTGCT     240

GTCAACGGCT GGGTCGGCAT GCCTGGTCGA ATCCGCCGGG AGTTCCCCGA CCAAGGCCGT     300

GGGGATTTCC GCATCCCCGC CGTTCGTATT CGGGAATCGG CAGGTTATAC TGCTGTCACA     360

ACTTTGGTAG TCCATCTGTA TGACAACTAT AGCTCCGTCG CGGCCGACTT GTCATACTCC     420

ATATTTCCGA AATATGATGC GATCGTGAGG AGTGTCAATG TGATCAACCA GGGCCCAGGT     480

AATATCACTA TCGAGGCCCT TGCAAGCATA AGTATCGATT TCCCCTATGA AGACCTCGAC     540
```

-continued

```
ATGGTCAGCC TCCGAGGCGA CTGGGCCAGA GAGGCAAATG TTCAGAGAAG CAAAGTGCAG    600

TATGGCGTCC AGGGATTCGG AAGCAGTACT GGATATTCCT CTCACCTTCA CAATCCCTTC    660

CTTGCCATAG TAGATCCAGC TACTACCGAA TCGCAAGGCG AGGCATGGGG TTTCAACCTT    720

GTATATACCG GCTCTTTCTC GGCCCAAGTA GAGAAAGGAT CGCAAGGTTT CACCCGGGCG    780

CTGCTCGGCT TCAACCCGGA CCAATTATCG TGGAACCTTG GCCCTGGCGA GACTTTAACT    840

TCCCCCGAGT GTGTTGCAGT CTACTCGGAC AAAGGCCTTG GCTCAGTGTC TCGCAAATTC    900

CACCGGCTAT ATCGCAACCA CCTCATGAAG AGCAAGTTCG CCACGTCCGA CCGGCCGGTT    960

CTGCTGAATA GCTGGGAAGG TGTTTATTTC GACTACAATC AAAGCAGCAT CGAAACTCTT   1020

GCCGAAGAGT CCGCTGCCCT GGGTGTCCAC CTCTTTGTCA TGGACGACGG CTGGTTTGGG   1080

GACAAGTACC CTCGAGTGTC CGATAACGCC GGACTGGGCG ACTGGATGCC CAATCCAGCG   1140

CGCTTGCCGG ACGGGTTGAC CCCGGTCGTG CAAGACATCA CAAATCTCAC CGTCAATGGC   1200

ACAGAGTCCA CAAAACTTCG CTTTGGTATT TGGGTGGAGC CCGAGATGGT CAACCCCAAT   1260

TCCACTCTCT ACCACGAACA CCCGGAGTGG GCGCTTCATG CCGGGCCTTA CCCCCGTACC   1320

GAGCGTCGGA ACCAGCTCGT CCTCAACCTG GCGCTTCCGG CTGTGCAGGA CTTCATCATA   1380

GACTTCATGA CGAACCTGTT ACAAGATACC GGCATTTCCT ACGTCAAATG GGACAACAAC   1440

CGGGGAATAC ACGAGACGCC CTCTCCGTCG ACTGACCATC AGTACATGCT TGGCCTCTAC   1500

CGGGTGTTCG ACACACTGAC CACCCGCTTC CCGGATGTCC TGTGGGAAGG ATGTGCCTCG   1560

GGTGGAGGCC GCTTTGATGC TGGCATGCTG CAGTATGTCC CCCAGATCTG GACTTCCGAT   1620

AACACCGACG CCATCGACCG AATCACCATC CAATTTGGGA CCTCGCTTGC CTACCCGCCA   1680

TCAGCAATGG GTGCCCACCT CTCCGCGGTT CCTAACGCAC AGACCGGTCG CACTGTGCCC   1740

ATTACTTTCC GCGCACACGT TGCTATGATG GGTGGTTCTT TCGGCTTGGA GCTGGATCCG   1800

GCGACGGTGG AAGGGGACGA AATAGTTCCC GAGCTTCTTG CGCTGGCGGA AAAAGTGAAC   1860

CCTATCATTT TGAACGGAGA TCTGTATCGG CTACGCCTAC CTCAAGACTC CCAGTGGCCT   1920

GCAGCACTCT TTGTGACTCA GGATGGCGCA CAGGCTGTTC TGTTCTACTT CCAGGTGCCA   1980

GCCGAATGTC AACCATGCCG TGCCGTGGGT CAGGCTGCAG GGGTTGGACC CTAA         2034
```

(2) INFORMATION FOR SEQ ID NO: 3:

(i) SEQUENCE CHARACTERISTICS:
        (A) LENGTH: 677 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

```
Met Ile Gly Leu Pro Met Leu Trp Cys Leu Gly Leu Phe Thr Leu Tyr
 1               5                  10                  15

Gly His Ser Ala Asp Thr Pro Ala Thr Gly Val Ser Asn Pro Gln Thr
            20                  25                  30

Ile Val Thr Asn Gly Thr Ser Phe Arg Leu Asn Gly Asp Asn Val Ser
        35                  40                  45

Tyr Arg Phe His Val Asn Ser Thr Thr Gly Asp Leu Ile Ser Asp His
    50                  55                  60

Phe Gly Val Val Ser Gly Thr Ile Pro Ser Pro Val Glu Pro Ala
65                  70                  75                  80

Val Asn Gly Trp Val Gly Met Pro Gly Arg Ile Arg Arg Glu Phe Pro
```

-continued

```
                        85                      90                      95
Asp Gln Gly Arg Gly Asp Phe Arg Ile Pro Ala Val Arg Ile Arg Glu
                    100                     105                     110

Ser Ala Gly Tyr Thr Ala Val Thr Thr Leu Val His Leu Tyr Asp
                115                     120                     125

Asn Tyr Ser Ser Val Ala Ala Asp Leu Ser Tyr Ser Ile Phe Pro Lys
            130                     135                     140

Tyr Asp Ala Ile Val Arg Ser Val Asn Val Ile Asn Gln Gly Pro Gly
145                     150                     155                     160

Asn Ile Thr Ile Glu Ala Leu Ala Ser Ile Ser Ile Asp Phe Pro Tyr
                    165                     170                     175

Glu Asp Leu Asp Met Val Ser Leu Arg Gly Asp Trp Ala Arg Glu Ala
                180                     185                     190

Asn Val Gln Arg Ser Lys Val Gln Tyr Gly Val Gln Gly Phe Gly Ser
                195                     200                     205

Ser Thr Gly Tyr Ser Ser His Leu His Asn Pro Phe Leu Ala Ile Val
            210                     215                     220

Asp Pro Ala Thr Thr Glu Ser Gln Gly Glu Ala Trp Gly Phe Asn Leu
225                     230                     235                     240

Val Tyr Thr Gly Ser Phe Ser Ala Gln Val Glu Lys Gly Ser Gln Gly
                    245                     250                     255

Phe Thr Arg Ala Leu Leu Gly Phe Asn Pro Asp Gln Leu Ser Trp Asn
                260                     265                     270

Leu Gly Pro Gly Glu Thr Leu Thr Ser Pro Glu Cys Val Ala Val Tyr
            275                     280                     285

Ser Asp Lys Gly Leu Gly Ser Val Ser Arg Lys Phe His Arg Leu Tyr
            290                     295                     300

Arg Asn His Leu Met Lys Ser Lys Phe Ala Thr Ser Asp Arg Pro Val
305                     310                     315                     320

Leu Leu Asn Ser Trp Glu Gly Val Tyr Phe Asp Tyr Asn Gln Ser Ser
                    325                     330                     335

Ile Glu Thr Leu Ala Glu Glu Ser Ala Leu Gly Val His Leu Phe
                340                     345                     350

Val Met Asp Asp Gly Trp Phe Gly Asp Lys Tyr Pro Arg Val Ser Asp
            355                     360                     365

Asn Ala Gly Leu Gly Asp Trp Met Pro Asn Pro Ala Arg Leu Pro Asp
            370                     375                     380

Gly Leu Thr Pro Val Val Gln Asp Ile Thr Asn Leu Thr Val Asn Gly
385                     390                     395                     400

Thr Glu Ser Thr Lys Leu Arg Phe Gly Ile Trp Val Glu Pro Glu Met
                    405                     410                     415

Val Asn Pro Asn Ser Thr Leu Tyr His Glu His Pro Glu Trp Ala Leu
                420                     425                     430

His Ala Gly Pro Tyr Pro Arg Thr Glu Arg Arg Asn Gln Leu Val Leu
            435                     440                     445

Asn Leu Ala Leu Pro Ala Val Gln Asp Phe Ile Ile Asp Phe Met Thr
                450                     455                     460

Asn Leu Leu Gln Asp Thr Gly Ile Ser Tyr Val Lys Trp Asp Asn Asn
465                     470                     475                     480

Arg Gly Ile His Glu Thr Pro Ser Pro Ser Thr Asp His Gln Tyr Met
                    485                     490                     495

Leu Gly Leu Tyr Arg Val Phe Asp Thr Leu Thr Thr Arg Phe Pro Asp
                500                     505                     510
```

```
Val Leu Trp Glu Gly Cys Ala Ser Gly Gly Arg Phe Asp Ala Gly
    515                 520                 525

Met Leu Gln Tyr Val Pro Gln Ile Trp Thr Ser Asp Asn Thr Asp Ala
    530                 535                 540

Ile Asp Arg Ile Thr Ile Gln Phe Gly Thr Ser Leu Ala Tyr Pro Pro
545                 550                 555                 560

Ser Ala Met Gly Ala His Leu Ser Ala Val Pro Asn Ala Gln Thr Gly
                565                 570                 575

Arg Thr Val Pro Ile Thr Phe Arg Ala His Val Ala Met Met Gly Gly
                580                 585                 590

Ser Phe Gly Leu Glu Leu Asp Pro Ala Thr Val Glu Gly Asp Glu Ile
            595                 600                 605

Val Pro Glu Leu Leu Ala Leu Ala Glu Lys Val Asn Pro Ile Ile Leu
    610                 615                 620

Asn Gly Asp Leu Tyr Arg Leu Arg Leu Pro Gln Asp Ser Gln Trp Pro
625                 630                 635                 640

Ala Ala Leu Phe Val Thr Gln Asp Gly Ala Gln Ala Val Leu Phe Tyr
                645                 650                 655

Phe Gln Val Pro Ala Glu Cys Gln Pro Cys Arg Ala Val Gly Gln Ala
                660                 665                 670

Ala Gly Val Gly Pro
            675

(2) INFORMATION FOR SEQ ID NO: 4:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Gly Ala His Leu Ser Ala Val Pro Asn Ala Gln Thr Gly Arg Thr Val
1               5                   10                  15

Pro Ile Thr Phe Arg Ala His Val
            20

(2) INFORMATION FOR SEQ ID NO: 5:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Asp Asp Gly Trp Phe Gly Asp Lys Tyr Pro Arg Val Ser Asp Asn Ala
1               5                   10                  15

Gly Leu Gly Asp Asp
            20

(2) INFORMATION FOR SEQ ID NO: 6:

(i) SEQUENCE CHARACTERISTICS:
        (A) LENGTH: 9 amino acids
        (B) TYPE: amino acid
        (C) STRANDEDNESS: single
```

(D) TOPOLOGY: linear (ii) MOLECULE TYPE: peptide (xi) SEQUENCE DESCRIPTION: SEQ ID NO: 6:

Thr Thr Arg Phe Pro Asp Val Leu Trp
1               5

(2) INFORMATION FOR SEQ ID NO: 7:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 7:

Thr Ser Asp Asn Thr Asp Ala Ile Asp Arg Ile Thr Ile Gln Phe
1               5                   10                  15

(2) INFORMATION FOR SEQ ID NO: 8:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 8:

Arg Leu Arg Leu Pro Gln Asp Ser Gln Trp Pro Ala Ala Leu Phe
1               5                   10                  15

(2) INFORMATION FOR SEQ ID NO: 9:

(i) SEQUENCE CHARACTERISTICS:
            (A) LENGTH: 18 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 9:

Gly Leu Glu Leu Asp Pro Ala Thr Val Glu Gly Asp Glu Ile Val Pro
1               5                   10                  15

Glu Leu (2) INFORMATION FOR SEQ ID NO: 10:

(i) SEQUENCE CHARACTERISTICS:
            (A) LENGTH: 19 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 10:

Val Met Asp Asp Gly Trp Phe Gly Asp Lys Tyr Pro Arg Val Ser Asp
1               5                   10                  15

Asn Ala Gly (2) INFORMATION FOR SEQ ID NO: 11:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

Val Met Asp Asp Gly Trp Phe Gly Asp Lys Tyr Pro Arg Val Ser Asp
1               5                   10                  15

Asn Ala Gly Leu Gly Asp Asp
            20

(2) INFORMATION FOR SEQ ID NO: 12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

TTACTAGTNA TGGAYGAYGG NTGGTT                                        26

(2) INFORMATION FOR SEQ ID NO: 13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

TTGAGCTCRT CNCCYAANCC NGCRTT                                        26

(2) INFORMATION FOR SEQ ID NO: 14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

TTGAGCTCRT CNCCNAGNCC NGCGTT                                        26

(2) INFORMATION FOR SEQ ID NO: 15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

TTGAGCTCRT CNCCNAGNCC NGCATT                                        26

(2) INFORMATION FOR SEQ ID NO: 16:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO: 16:

GCGTTATCGG ACACTCG                                               17

(2) INFORMATION FOR SEQ ID NO: 17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

GTTTGGGGAC AAGTACC                                               17

(2) INFORMATION FOR SEQ ID NO: 18:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

CTGCAGTCGA CTCTAGAGGA TCCGCGGCCG CTTTTTTTTT TTTTTTTTT TTTTT      55

(2) INFORMATION FOR SEQ ID NO: 19:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

TTACTGCAGT CGACTCTAGA GGATCCGCG                                  29

(2) INFORMATION FOR SEQ ID NO: 20:

(i) SEQUENCE CHARACTERISTICS:
        (A) LENGTH: 106 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

GCTCCTCATG GTGGATCCCC AGTTGTGTAT ATAGAGGATT GAGGAAGGAA GAGAAGTGTG      60

GATAGAGGTA AATTGAGTTG GAAACTCCAA GCATGGCATC CCTTGC                    106

(2) INFORMATION FOR SEQ ID NO: 21:

(i) SEQUENCE CHARACTERISTICS:

```
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

TGTTCTGGCT GTGGTGTACA GG                                                  22

(2) INFORMATION FOR SEQ ID NO: 22:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

GCAAGCTTTA TCATCACCAC CATGAT                                              26
```